United States Patent [19]

Flemer, III

[11] Patent Number: Plant 7,203

[45] Date of Patent: Mar. 27, 1990

[54] *AMELANCHIER LAEVIS* "MAJESTIC"

[75] Inventor: William Flemer, III, Princeton, N.J.

[73] Assignee: Newplant Associates, Princeton, N.J.

[21] Appl. No.: 291,968

[22] Filed: Dec. 30, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

An *Amelanchier laevis* tree having exceptionally vigorous growth, reaching twice the height of prior known *Amelanchier laevis* trees during the same growth period, the growth being tall and narrow, blooms exhibiting long, drooping racemes with many white flowers, new foliage of dark, reddish orange color becoming thick and dark green, as they mature, with resistance to hot, humid weather.

2 Drawing Sheets

DESCRIPTION OF THE INVENTION

This invention relates to an *Amelanchier laevis* tree and is particularly directed to the unique ornamental characteristics of the tree as well as its resistance to damage in hot, humid weather.

As a part of a long continuing program of development of ornamental trees in general and particularly those which are different from usual ornamental trees, a substantial part of a nursery near Princeton, N.J., to which I have access, is devoted to growing and selecting trees which have outstanding characteristics, setting them apart from those heretofore available.

One result of this program to which I devote substantial time and effort, is the instant *Amelanchier laevis* tree which was discovered in a nursery row of seedlings of the variety, which seedling is particularly vigorous, evidenced by the fact that at four years of age, this seedling was about twice the height of sibling seedlings in the same row.

Depending upon the weather during the growing season, my new variety grafted trees grow from one-third faster to one-half faster than ordinary *Amelanchier laevis* seedlings cut back and growing in adjacent rows. In a recent year despite the drought, lightly branched trees of one summer's growth were 6 to 7 feet tall, a truly remarkable growth rate for this tree in the New Jersey climate where grown.

The parent tree shown at eleven years of age, was 28 feet tall.

A further distinctive aspect of my new variety is that when it blooms, it exhibits long, drooping racemes, 12 to 15 centimeters in length when fully mature, with abundant large, white flowers. The new foliage produced is a colorful dark reddish orange color, and such foliage becomes leaves which are thick and dark green. Further the leaves are retained undamaged in hot, humid weather when other amelanchier trees in the same block are severely defoliated.

The foregoing characteristics, taken together with the tall, narrow growth habit exhibited, have influenced me to select the name 'Majestic' by which the trees will be identified in the trade.

I have found that asexual reproduction of my new variety by grafting on bare root understocks, established that the characteristics set forth heretofore, come true in successive generations and provide a desirable commercial ornamental trees.

Details of the characteristics of my new variety by which the same may be identified are disclosed in the following detailed description and shown in the drawing which discloses the tree in full bloom and in color as nearly as possible like that of the actual tree, and using a color photograph, the observations being made as to color in daylight and as compared with the Nickerson Color Fan, produced by Munsell Color Company using notations set forth therein.

The second drawing discloses the distinctive red color of the expanding foliage wherein the leaves turn dark green when mature.

The raceme disclosed is not as fully expanded as it will be ultimately, but when it is, it becomes heavy enough to cause the raceme to bend downwardly and thus be moderately pendulous.

DETAILED DESCRIPTION OF THE INVENTION

Parentage:

*Seed parent.*—*Amerlanchier laevis* Princeton Selection No. 9.

*Pollen parent.*—Unknown.

Tree: Medium, widespread, upright, tall, (parent tree now 28 feet, 8.53 meters), and hardy.

*Trunk.*—Slender, smooth, pale grey and about 17.31 cm in diameter when fully grown.

*Branches.*—Number — Many growing fromn close to ground (1.32 m). Width — About 6.40 m. Slender and smooth. Color — Moderate brown 7.5 YR 4/5. Lenticels — Very few.

*Leaves.*—Exceptionally large, very thick. Quantity — Moderately abundant. Length — 12 cm. Width — 6 cm. Shape — Ovate oblong, shortly acuminate, rounded base. Color — When expanding in spring ½ and ⅔ expanded—standard red 5R4/12 and then — dark reddish orange 7.5R 4/11. Fall color — Vivid red 5R 5/13. Summer — Upper surface dark yellowish green 2.5G 3/3. Under surface moderate olive green 2.5GY 4/3.

*Margin.*—Serrate.

*Petiole.*—Medium; 4 cm long.

*Glands.*—None.

Flower buds: Very hardy. 1.1 cm long.

*Shape.*—Ovate; acuminate.

Flowers: Borne in many flowered, drooping racemes, 12 to 14 flowers per raceme. Dates first bloom: April 10. full bloom: April 15.

*Quantity.*—Abundant.

*Size.*—Large.

Petalage: Number of petals 5.

*Shape of petals.*—Narrow oval with rounded tips.

*Size of petals.*—Length 2 cm. Width 0.6 cm.

*Color.*—White.

Fruits:

*When borne.*—Mid June.

*Abundance.*—Abundant.

*Size.*—Globose, 1.2 cm wide, 1 cm long.

*Color.*—Dark purple.

I claim:

1. A new and distinct variety of *Amelanchier leavis* tree, substantially as herein shown and described, characterized particularly as to novelty by its vigorous, narrow, tall, growth habit, such growth being usually twice as rapid as other *Amelanchier laevis* trees, its long, drooping racemes with blooms of abundant white flowers, colorful new foliage of dark reddish orange color, becoming thick, dark green leaves as the leaves mature, which leaves are retained undamaged in hot, humid weather when defoliation of other nearby *Amelanchier laevis* trees takes place.

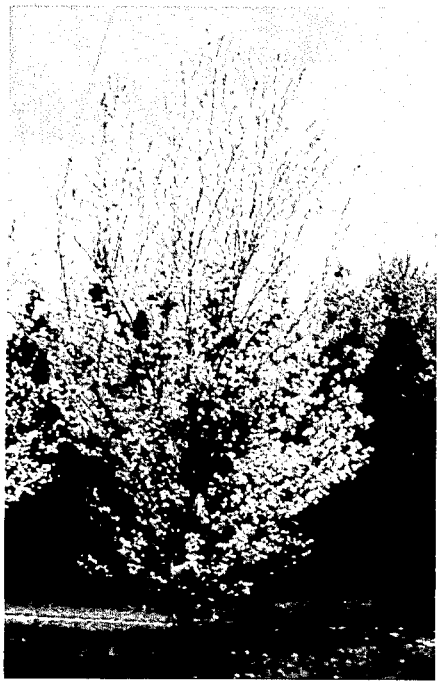

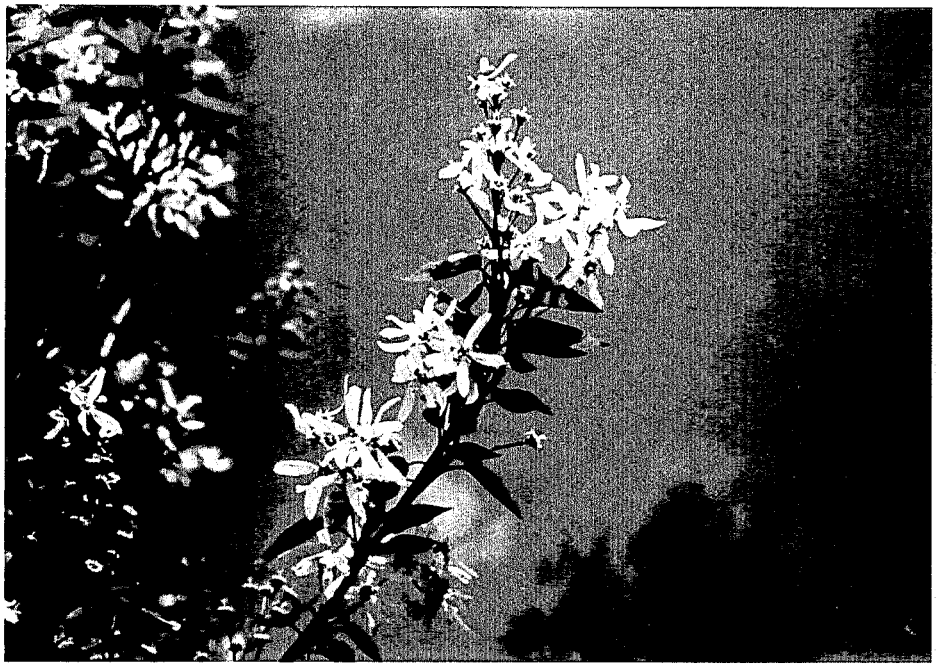

* * * * *